United States Patent [19]

Suzuki et al.

[11] Patent Number: 5,057,074
[45] Date of Patent: Oct. 15, 1991

[54] MEDICAL CONTAINER REPLACING METHOD

[75] Inventors: Kensuke Suzuki, Nagaoka; Norisuke Kira, Fujinomiya, both of Japan

[73] Assignee: Terumo Kabushiki Kaisha, Tokyo, Japan

[21] Appl. No.: 528,943

[22] Filed: May 25, 1990

[30] Foreign Application Priority Data

May 26, 1989 [JP] Japan .................. 1-133393

[51] Int. Cl.⁵ .................... A61M 5/14; A61M 25/00
[52] U.S. Cl. ......................... 604/49; 604/29
[58] Field of Search ................ 604/49, 29, 283

[56] References Cited

U.S. PATENT DOCUMENTS

| | | | |
|---|---|---|---|
| 4,190,047 | 2/1980 | Jacobsen et al. | 604/29 X |
| 4,439,179 | 3/1984 | Lueders et al. | 604/29 X |
| 4,440,207 | 4/1984 | Genatempo et al. | 604/905 X |
| 4,588,402 | 5/1986 | Igari et al. | 604/408 |
| 4,619,642 | 10/1986 | Spencer | 604/29 |
| 4,676,476 | 6/1987 | Herrli | 251/9 |
| 4,687,471 | 8/1987 | Twardowski et al. | 604/29 X |
| 4,745,950 | 5/1988 | Mathieu | 604/29 X |
| 4,772,269 | 9/1988 | Twardowski et al. | 604/29 X |
| 4,878,516 | 11/1989 | Mathieu | 604/29 X |

*Primary Examiner*—William H. Grieb
*Attorney, Agent, or Firm*—Frishauf, Holtz, Goodman & Woodward

[57] ABSTRACT

Peritoneal dialysis uses a system comprising (A) a first tube having a first connector attached thereto at one end and (B) a second tube connected to a dialysis fluid bag and having a second connector attached thereto at a free end, both the first and second tubes requiring to be in a sterile condition when connected. A medical container may be replaced by connecting the first connector to the second connector to provide fluid communication between the first and second tubes for allowing dialysis to be carried out, sealing the second tube at one or more positions at the end of dialysis, and cutting the second tube at a position nearer to the medical container with respect to the seal. The suspending section of the second tube with the second connector kept connected to the first connector serves as an antibacterial protective accessary for maintaining the connector connection in a sterile condition.

5 Claims, 7 Drawing Sheets

MEDICAL CONTAINER REPLACING METHOD

FIELD OF THE INVENTION

This invention relates to a method for replacing a medical container for use in a medical treatment, typically peritoneal dialysis and requiring to be kept in a sterile condition.

BACKGROUND OF THE INVENTION

Peritoneal dialysis therapy has drawn greater attention than conventional dialysis using an artificial kidney because of a smaller and simpler form of system including equipment and instrument, a lower cost of treatment, possible prevention of abdominal adhesion, and a reduced burden to the patient.

Among the different versions of peritoneal dialysis, continuous ambulatory peritoneal dialysis often abbreviated as CAPD is regarded most promising because the patient himself or herself can replace a container or bag of dialysis fluid anywhere at home or office, assisting him or her in resuming work.

In the practice of CAPD, a catheter tube is left in the abdominal cavity of the patient, a transfer tube is connected to an outside end of the catheter tube, and a bag tube of an infusion bag full of dialysis fluid is connected to the transfer tube. Then the dialysis fluid is infused from the bag into the abdominal cavity through the tubes and catheter. After dialysis is carried out for a predetermined time, the dialysis fluid in the abdominal cavity is drained into a drainage bag through the tubes. The bag tube and the transfer tube are connected through male and female connectors attached to the tube end.

One and two bag systems are known in the CAPD. The one bag system uses one bag which serves both as an infusion bag for dialysis fluid and a drainage bag. This system imposes a trouble to the patient in that the patient must always carry an empty bag which has been an infusion bag and which is to be used as a drainage bag at the end of dialysis. The two bag system includes a parallel connection (known as a Y set) of an infusion bag for dialysis fluid and a drainage bag. This system allows the infusion and drainage bags to be separated from the transfer tube during dialysis, eliminating a need for carrying a bag.

Since the CAPD is a medical treatment to the abdominal cavity, that is, a site having no protection against bacteria, it is the most critical task to prevent bacterial entry into the respective tubes. Bacterial entry into the tubes can most often occur during connection and disconnection of the transfer tube and the bag tube. An important problem associated with the two bag system in which the bag tube is disconnected from the transfer tube during dialysis is how to prevent bacterial entry from the open end of the transfer tube.

For the prevention of bacterial entry, Japanese Patent Disclosure No. 500801/1984 corresponding to PCT/US83/00511 (based on U.S. application Ser. No. 378,315 filed May 14, 1982, (now U.S. Pat. No. 4,440,207) discloses an antibacterial protective cap adapted to mount on a connector. The cap includes two large and small continuous chambers adapted to accommodate the mating portion of a connector attached to the tube end. The outer large chamber on the inner wall is lined with an absorbent material carrying a disinfectant thereon. The key is to place the mating portion of the connector in contact with the disinfectant. This concept achieves a low level of sterilization by carrying out mere disinfection in the sense that disease-inducing bacteria are reduced or attenuated rather than a high level of sterilization capable of maintaining a sterile condition in the sense that all bacteria are completely killed. Iodide agents such as Isodine (trade mark, Meiji Seika K.K.) and povidone-iodine are often used as the disinfectant. Since the disinfectant, when mixed with the dialysis fluid, acts as a harmful substance to the human body, it must be diluted to a fully low concentration, resulting in lower biocidal activity. Therefore, the cap cannot completely prevent bacterial entry into the tube, leaving a safety problem.

SUMMARY OF THE INVENTION

Therefore, an object of the present invention is to provide a novel method for replacing a medical container while maintaining tubes in a sterile condition.

The present invention provides a method for replacing a medical container in a system comprising (A) a first tube having a first connector attached thereto at one end and (B) a second tube connected to a medical container and having a second connector attached thereto at a free end, both the first and second tubes requiring to be in a sterile condition when connected. The present method includes the steps of:

connecting the first connector to the second connector to provide fluid communication between the first and second tubes for allowing a medical treatment to be carried out, blocking the second tube at one or more transverse positions at the end of medical treatment, and cutting the second tube into suspending and separated sections at a position nearer to the medical container with respect to the blockade nearest to the second connector, the suspending section of the second tube with the second connector kept connected to the first connector serving as an antibacterial protective accessary for maintaining the connector connection in a sterile condition.

Preferably, two blockades are formed in the second tube and the tube is cut between the two blockades.

Preferably, the second tube is sealed by fusion welding or blocked by mechanical clamping means.

Preferably, the step of connecting the first and second connectors is carried out in a flame.

BRIEF DESCRIPTION OF THE DRAWINGS

The above and other objects, features and advantages of the present invention will be better understood from the following description taken in conjunction with the accompanying drawings.

DESCRIPTION OF THE PREFERRED EMBODIMENTS

The medical container replacement method of the invention will now be described in connection with a preferred system for use in continuous ambulatory peritoneal dialysis.

Figure 1:
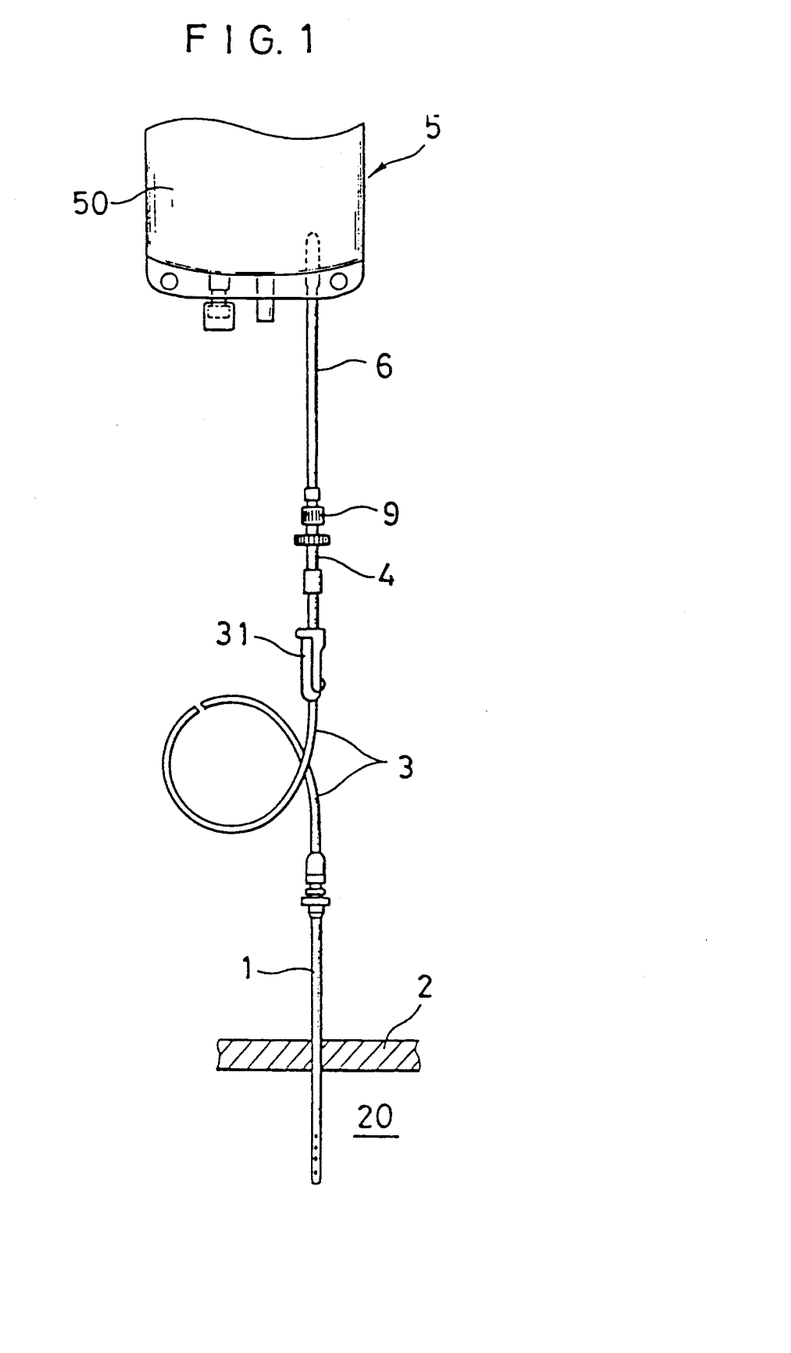
FIG. 1 is a plan view showing a typical system of tubes connected when the invention is applied to CAPD.

Referring to FIG. 1, there is illustrated a system of connected tubes desirable when the present invention is applied to peritoneal dialysis (CAPD). An abdominal catheter 1 is inserted through an abdominal wall 2 of the patient such that its distal portion is left within an abdominal cavity. The proximal end of the abdominal catheter 1 which is located outside the patient body is connected to one end of a transfer tube 3 through a connector or joint. A first connector 4 to be described later is attached to the transfer tube 3 at the other end. The transfer tube 3 in proximity to the first connector 4 is provided with a clamp 31 for blocking the transfer tube 3.

A container or bag 5 for containing a dialysis fluid to be infused or drained includes a bag body 50 and a bag tube 6 connected to the bag body 50 in communication with the interior thereof. The bag tube 6 at its free end is provided with a second connector 9 to be described later. It is to be noted that the bag 5 shown in FIG. 1 is an infusion bag for containing dialysis fluid.

When it is desired to infuse a dialysis fluid, the first connector 4 is mated with the second connector 9 to provide fluid communication between the transfer tube 3 and the bag tube 6 as shown in FIG. 1.

Figure 2:
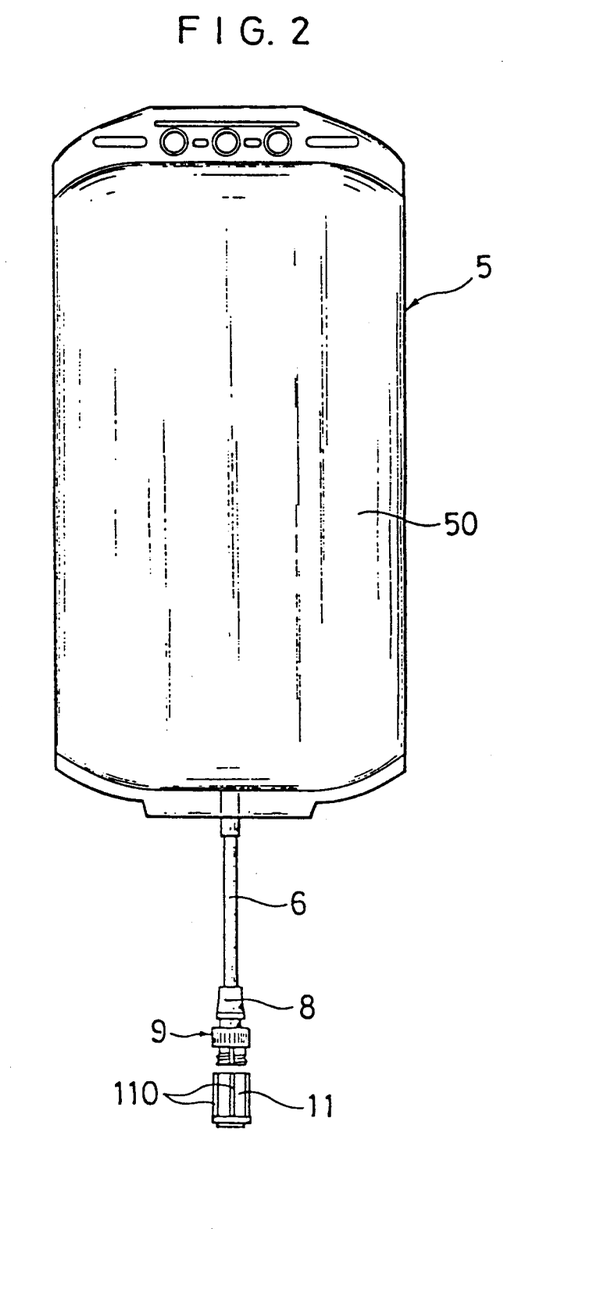
FIG. 2 is a plane view of a medical container in the form of a bag for dialysis fluid used in the system.

FIG. 2 is a plan view showing one example of a medical container or bag useful in the practice of the present invention. The bag 5 illustrated herein is a drainage bag for receiving a used dialysis fluid. The bag 5 includes a bag body 50, a bag tube 6 connected to the bag body 50 in communication with the interior thereof, and a second connector 9 attached to the bag tube 6 at its free end.

The bag body 50 includes a tubular sheet formed of a transparent resin such as polyvinyl chloride, ethylene-vinyl acetate copolymer (EVA), and polyethylene, which is sealed along opposite edges to form a bag. It has a sufficient volume of 300 to 2,000 ml to receive an amount of dialysis fluid (infusion or drainage).

The bag tube 6 is a flexible tube formed of a resin such as polyvinyl chloride, ethylene-vinyl acetate copolymer (EVA), and polyethylene. The bag tube 6 at one end is connected to the bag body 50 in a liquid tight seal to communicate with the interior of the bag body 50.

The bag tube 6 has a free end into which a spud of the second connector 9 is inserted. A fitting sleeve 8 is fitted over the bag tube free end and crimped to firmly engage the bag tube end portion to the second connector spud, thereby preventing disengagement of the second connector 9.

Figure 3:
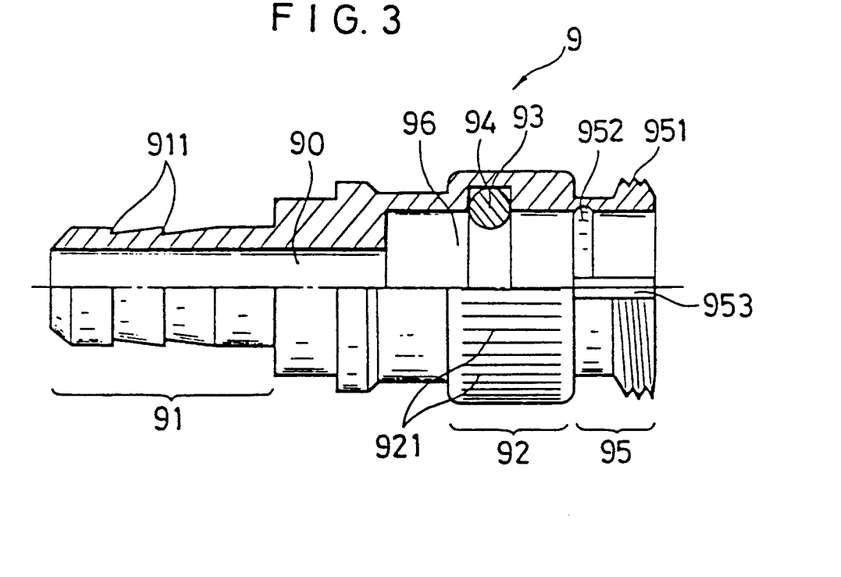
FIG. 3 is a partially cross-sectional side elevation of a second connector used in the system.

The construction of the second connector 9 is described in further detail. FIG. 3 is an enlarged side elevation of the second connector 9 showing an upper half portion thereof in axial cross-section. As seen from the figure, the second connector 9 is a female connector defining a flowpath 90 therethrough. The second connector 9 includes a spud 91, a grip portion 92, and a thread portion 95 as a one-piece member.

The second connector 9 includes the spud 91 adapted to be connected to the bag tube 6 at the left of the figure. The spud 91 is formed with serrations 911 for preventing disengagement of the bag tube 9.

The second connector 9 includes the grip portion 92 as a somewhat dilated portion at an intermediate which the human operator can grip upon connection or disconnection of the connector. The grip portion 92 is provided over the peripheral surface with a plurality of fine furrows 921 for anti-slip grip. The grip portion 92 defines inside a bore 96 having a larger diameter than the flowpath 90 defined in the spud 91. The grip portion 92 is internally formed with a circumferentially extending recess 93. An O-ring 94 is fitted in the recess 93 for providing a liquid tight seal through the flowpath 90 when the second connector 9 is mated with the first connector 4 to be described later. The O-ring 94 may be formed of a heat resistant elastomeric material such as silicone rubber.

The second connector 9 includes the thread portion 95 adjacent the grip portion 92 at the right in FIG. 3. The thread portion 95 is formed with external threads 951 from the rightmost end. The thread portion 95 defines inside a bore having substantially the same diameter as the grip portion bore 96. A circumferentially extending engagement groove 952 is formed in the bore 96 between the grip and thread portions 92 and 95. The thread portion 95 further includes axial slots 953 at diametrically opposite positions (only one slot 953 is seen in FIG. 3). The slots 953 are formed for imparting resilience to the thread portion 95, thereby allowing for easy engagement and disengagement between the groove 952 and a ridge 411 on the first connector 4 to be described later.

Figure 5:
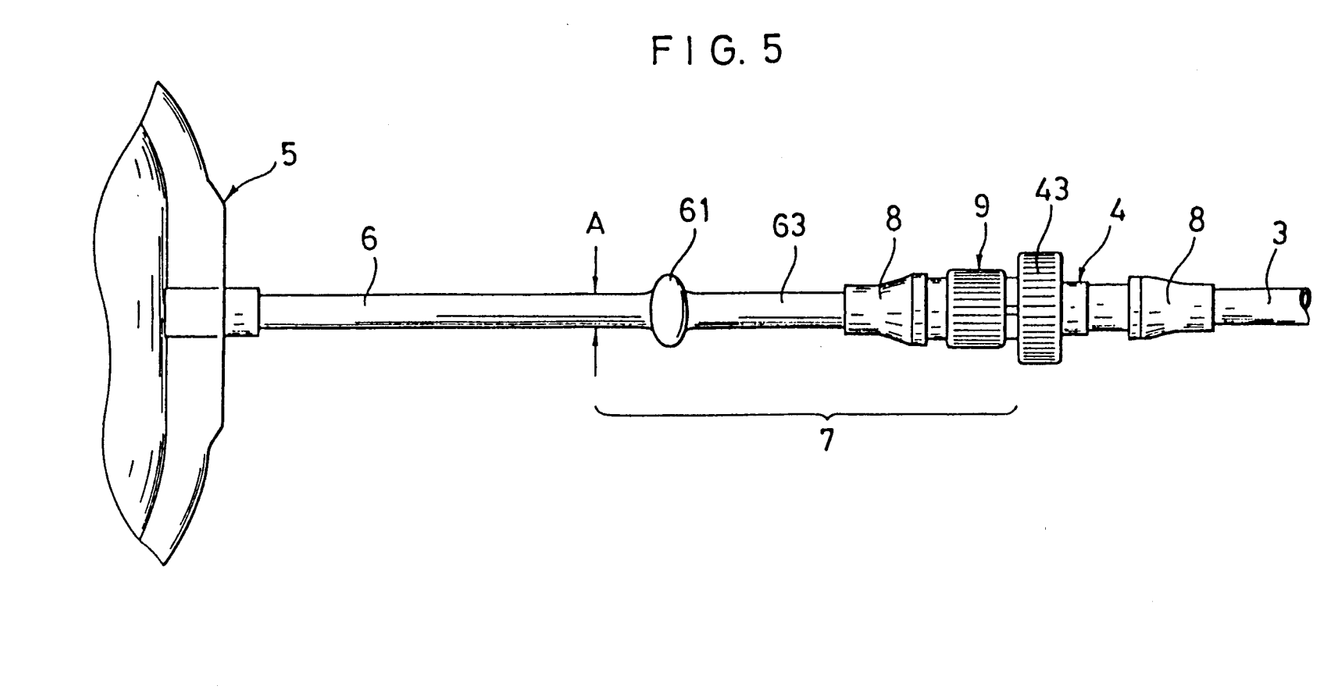
FIGS. 5, 6, and 7 are plan views showing different patterns of seals and different cutting positions in the bag tube.

As previously described, the second connector 9 is attached to the bag tube 6 by inserting the second connector spud 91 into the free end of the bag tube 6 and fastening the fitting sleeve 8 over the bag tube and the spud under pressure (see FIG. 5). It is to be noted that the fitting sleeve 8 is previously fitted over the end portion of the bag tube 6 and after insertion of the connector spud 91, shrunk and crimped thereto through a heat treatment. This crimping engagement prevents removal of the bag tube 6 from the connector spud 91, ensures a liquid tight seal, and inhibits bacterial entry. It will be understood that the operation of inserting the connector spud 91 into the bag tube 6 and crimping the fitting sleeve 8 is a very easy task.

When the bag tube 6 is not connected to the transfer tube 3, a sterile cap 11 is mounted on the second connector 9 for preventing entry of dust, debris and bacteria as shown in FIG. 2. The cap 11 is engaged with the second connector 9 so that the cap 11 covers at least the connector thread portion 95. The cap 11 may be formed of a resin such as polypropylene, polyvinyl chloride, and polyethylene. The cap 11 is formed on the outer periphery with a plurality of reinforcing ribs 110.

Figure 4:
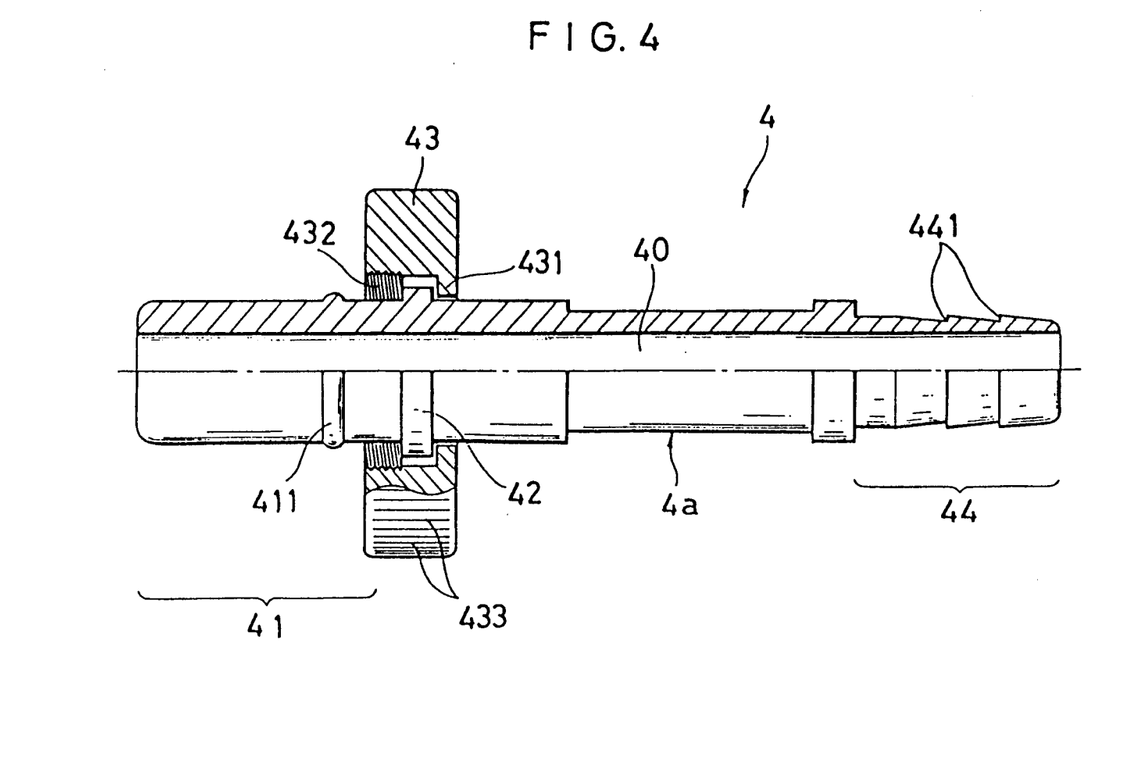
FIG. 4 is a partially cross-sectional side elevation of a first connector used in the system.

Next, the construction of the first connector 4 which is attached to the transfer tube 3 is described in detail. FIG. 4 is an enlarged side elevation of the first connector 4 showing an upper half portion thereof in axial cross-section. As seen from the figure, the first connector 4 is a male connector engageable with the second connector 9 and defining a flowpath 40 through a connector housing 4a. The first connector 4 includes a mating portion or projection 41, a thread portion, and a spud 44 as a one-piece member.

The first connector 4 includes the mating portion or projection 41 at the left in FIG. 4 which is to be inserted into the bore 96 of the second connector 9. The length of the projection 41 is substantially equal to or slightly shorter than the axial distance of the second connector bore 96. The projection 41 is formed on the outer periphery with a circumferentially extending ridge 411 adapted to engage with the groove 952 in the second connector 9. The ridge 411 is located so as to register with the groove 952 when the projection 41 is inserted into the second connector bore 96.

A circumferentially extending flange 42 is formed at the rightmost end of the projection 41. A ring 43 is fitted over the flange 42 for free rotation about the connector housing 4a. The ring 43 includes an annular inner collar 431 at the right end, the collar 431 having an inner diameter larger than the outer diameter of the connector housing 4a, but smaller than the outer diameter of the flange 42. At the left, the ring 43 has internal threads 432 adapted to engage with the external threads 951 of the second connector 9. The ring 43 is formed on the outer periphery with a plurality of fine furrows 433 for anti-slip grip.

The first connector 4 further includes the spud 44 adapted to be connected to the transfer tube 3 at the right in FIG. 4. The spud 44 is also formed with serrations 441 for preventing disengagement of the transfer tube 3.

The first connector 4 is attached to the transfer tube 3 by inserting the first connector spud 44 into the free end of the transfer tube 3 and fastening the fitting sleeve 8 over the transfer tube and the spud under pressure (see FIG. 5).

In order that the first and second connectors 4 and 9 be connected in a flame, they are preferably formed of a refractory material. The connector materials are preferably refractory and corrosion resistant and include metal materials such as stainless steel, titanium alloy, Hastelloy, and Inconel and ceramic materials such as alumina, silica, and silicon nitride, and mixtures thereof. The connector may also be made of any of the above and other metals which is plated with a coating of Cr, Ni, or an alloy thereof for improving corrosion resistance.

It should be appreciated that the first and second connectors 4 and 9 may be formed of the same or different materials. For example, the first and second connectors 4 and 9 are formed from materials having different coefficients of thermal expansion to such dimensions that the first connector projection 41 may be smoothly inserted into the second connector bore 96 when the connectors are heated (or to be connected), but the first connector projection 41 may snugly fit in the second connector bore 96 without a gap when the connectors are cooled to room temperature because the second connector 9 (or bore 91) contracts at a greater rate than the first connector 4 (or projection 41). This ensures a liquid tight seal at the connection between the first and second connectors 4 and 9 and complete inhibition of bacterial entry. In this example, the connectors must be heated again before they can be disconnected.

With the above-mentioned constructions of the first and second connectors 4 and 9, the connectors can be readily engaged and disengaged while maintaining a sterile condition at the connection therebetween.

The foregoing description is made for illustrative purposes only. The first and second connectors 4 and 9 are not limited to the illustrated structures. For example, the connectors may take any of the frame lock structures shown in Japanese Patent Application Kokai No. 211353/1982.

The method for replacing a medical container according to the present invention will be described by referring to the replacement of a bag used in CAPD.

The bag tube 6 of the infusion fluid bag 5 is connected to the transfer tube 3 as shown in FIG. 1 by engaging the first and second connectors 4 and 9 together. This procedure is described below with reference to FIG. 5.

First, the sterile cap 11 is disengaged from the second connector 9 as shown in FIG. 2. The projection 41 of the first connector 4 is inserted into the bore 96 of the second connector 9. When the projection 41 is forced into the bore 96 to some extent, the thread portion 95 comes in substantial register with the ring 43. Then the ring 43 is turned in a predetermined direction to engage the external threads 951 on the thread portion 95 with the internal threads 432 in the ring 43. With this thread engagement, the ring 43 is moved toward the second connector 9 (to the left in FIG. 5). The collar 431 of the ring 43 abuts against the flange 42, the ring 43 on turning forces the connector housing 4a toward the second connector 9. In this way, the first connector projection 41 gradually advances deeply into the first connector bore 96.

When the first connector projection 41 is deeply inserted into the second connector bore 96, the ridge 411 on the projection 41 snugly fits in the groove 952 in the bore 96, achieving proper positioning of the first and second connectors 4 and 9. At this point, the connection or engagement between the first and second connectors 4 and 9 is completed, providing fluid communication between the flowpaths 90 and 40 of the connectors.

With the first connector projection 41 inserted in the second connector bore 96, the O-ring 94 is in pressure and close contact with the projection 41 over its entire circumference, ensuring a liquid tight seal between the connectors and inhibiting bacterial entry.

The above-mentioned operation of engaging the first and second connectors 4 and 9 is carried out in a flame, especially in a reducing flame of an alcohol lamp, for example. Then, the connectors are sterilized during their engagement, ensuring maintenance of a sterile condition within the associated tubes. Preferably, the connectors are heated to a temperature of about 150° to about 300° C. for about 10 to about 30 seconds.

After the first and second connectors 4 and 9 are tightly engaged in this way, the infusion fluid bag 5 is suspended at a higher position. Then the system is ready for a medical treatment, that is, the dialysis fluid in the bag 5 is infused into the patient's abdominal cavity 20 through the bag tube 6, transfer tube 3, and the abdominal catheter 1.

Figure 6:
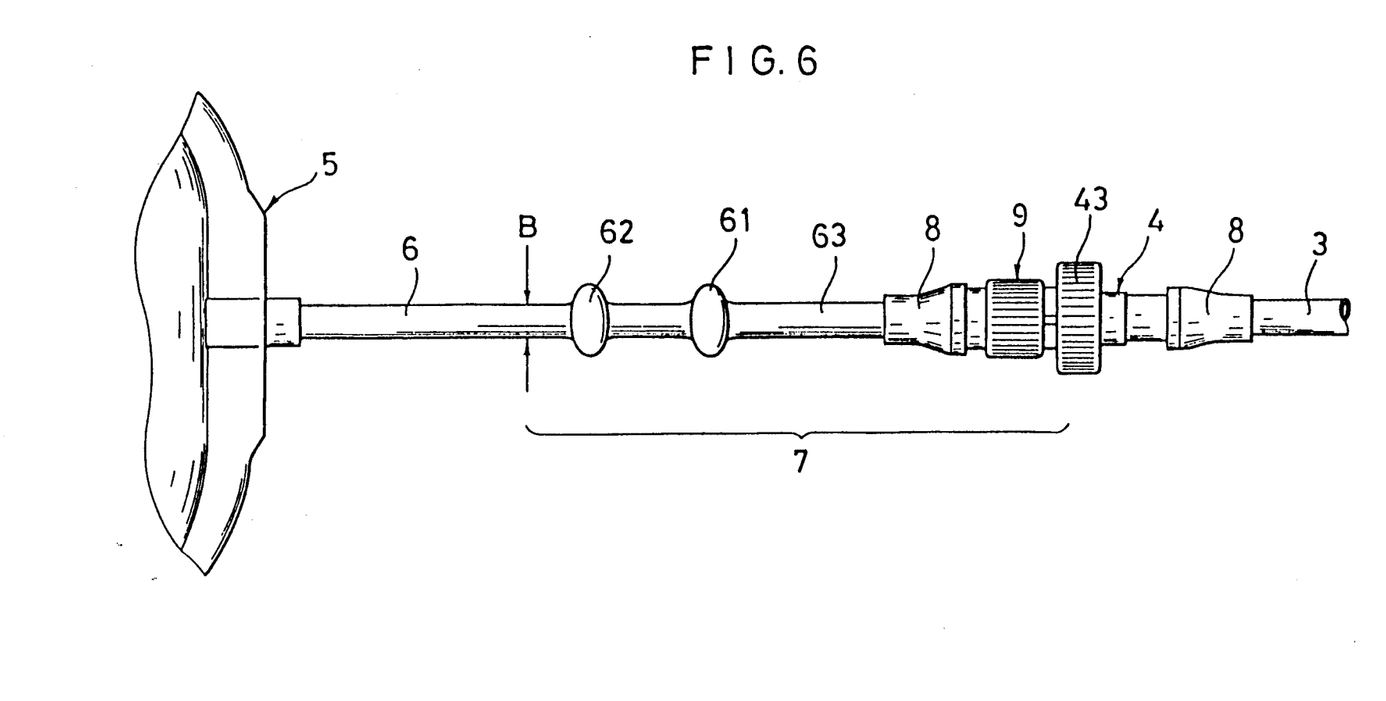
Figure 7:
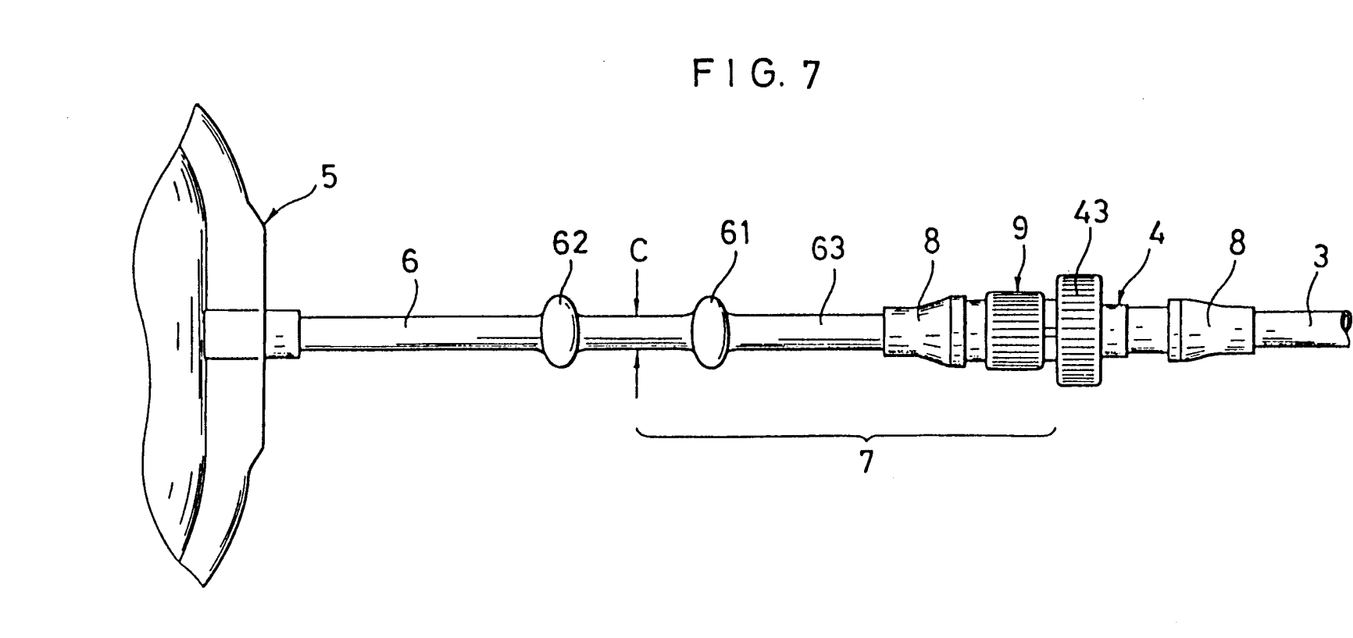

When the infusion of dialysis fluid into the abdominal cavity is completed, the transfer tube 3 is pinched by the clamp 31 to prevent reverse flow of the dialysis fluid. Then the bag tube 6 is blocked at one or more positions by suitable clamping or sealing means to form a seal 61 (FIG. 5) or seals 61 and 62 (FIGS. 6 and 7). The bag tube 6 is cut at a position near to the bag 5 with respect to the seal 61 which is nearest to the second connector 9.

FIGS. 5 to 7 show different patterns of seal formation and the position of such a tube cut. In the first example of FIG. 5, the seal 61 is formed in the bag tube 6 at a single position which is spaced about 30 to about 150 mm from the tube end, for example. The bag tube 6 is cut at a position A near to the bag 5 with respect to the seal 61. The thus separated bag 5 is discarded. In turn, on the side extending from the cut position A to the second connector 9, there remains a short section 63 of the bag tube with the second connector 9. This remaining or suspending section 63 with the second connector 9 is utilized as an antibacterial protective accessary depicted at 7. That is, bacterial entry from the cut end of the section 63 of the bag tube is inhibited by the seal 61 while the inhibition of bacterial entry at the connection between the first and second connectors 4 and 9 is maintained as previously described.

In the second example of FIG. 6, first and second seals 61 and 62 are formed in the bag tube 6 at two positions. The first seal 61 is located nearer to the connector 9 than the second seal 62. The bag tube 6 is cut at a position B near to the bag 5 with respect to the second seal 62. Then the suspending section 63 of the bag tube serving as the protective accessary 7 contains the two seals 61 and 62, providing double protection against bacterial entry.

In the third example of FIG. 7, first and second seals 61 and 62 are formed in the bag tube 6 at two positions, the first seal 61 being located nearer to the connector 9 than the second seal 62 as in the second example. The bag tube 6 is cut at a position C between the first and second seals 61 and 62. The advantage associated with the suspending section 63 of the tube bag is the same as in the first example. In this third example, the cut-off section of the tube bag 6 associated with the bag 5 is also closed at the seal 62, preventing the dialysis fluid from leaking out of the bag 5 before the bag is discarded. This is convenient particularly when the bag 5 is a drainage bag which is filled with a used dialysis fluid. Leakage of such used dialysis fluid from the separated bag 5 is prevented until the fluid can be discharged to a toilet or proper drain.

Of course, the seal forming pattern and the cut position are not limited to the examples illustrated in FIGS. 5 to 7.

Seals (seals 61 and 62) are preferably formed in the bag tube 6 by a fusion welding technique such as thermal sealing or ultrasonic sealing because such a technique can readily provide tight seals.

Figure 8:
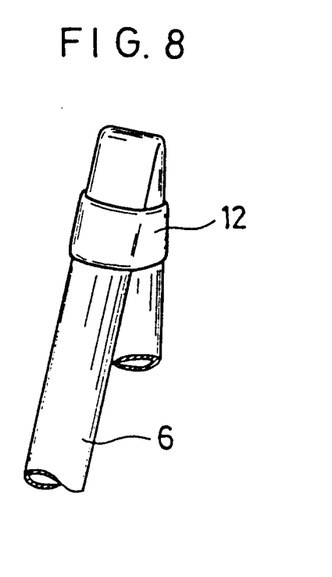
FIGS. 8 and 9 are perspective views of different examples of mechanical clamping means.
Figure 9:
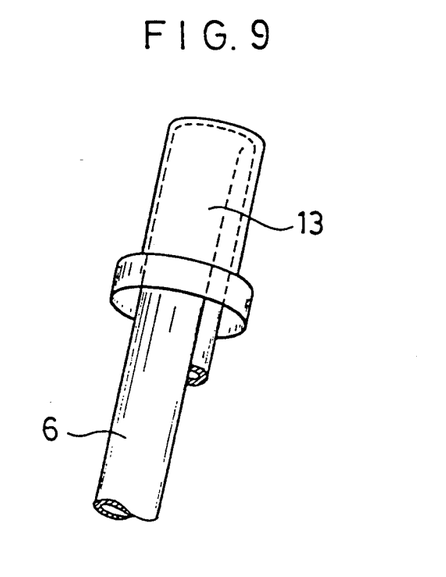

Alternatively, the tube can be blocked by folding the tube and securing the folded tube sections in tight pressure contact by means of a fastener, for example, an annular band 12 as shown in FIG. 8 and a cylindrical fixture 13 as shown in FIG. 9. The band 12 and fixture 13 may be formed from collapsible metal such as aluminum and brass. It is also possible to block the tube by means of a clamp or fastening member without folding the tube.

During dialysis, the cut section 63 of the bag tube as the protective accessary 7 remains connected to the other end of the transfer tube 3. The protective accessary 7 which consists of the suspending section 63 and the second connector 9 is of a relatively small size causing minimal trouble to the patient as compared with the conventional situation wherein an empty bag remains connected. Unlike simple disinfection, the protective accessary 7 ensures that the tube interior is maintained sterile, offering increased safety to the patient.

After dialysis, the fluid is discharged from within the abdominal cavity by disengaging the protective accessary 7 from the transfer tube 3 and engaging a bag tube 6 of a new drainage bag 5 to the transfer tube 3.

More particularly, the first and second connectors 4 and 9 are disengaged by reversing the above-mentioned operation of engaging the connectors. The first connector ring 43 is turned in the reverse direction to disengage the internal threads 432 from the external threads 951 on the second connector thread portion 95. While the second connector grip portion 92 is grasped with fingers, the first connector 4 is withdrawn from the second connector 9 (to the right in FIG. 4), thereby separating the protective accessary 7 from the transfer tube 3.

The disengagement of the first and second connectors 4 and 9 may or may not be carried out in a flame. Whether or not disengagement is done in a flame is determined depending on the connector type and construction.

After the protective accessary 7 is separated from the transfer tube 3, the bag tube 6 of the drainage bag 5 is connected to the transfer tube 3 by engaging the second connector 9 at the end of the bag tube 6 with the first connector 4 at the end of the transfer tube 3. This engagement is done in the same manner as previously described for the infusion bag.

After the bag tube 6 is connected to the transfer tube 3, the clamp 31 is released and the drainage bag 5 is located at a lower position. Then the system is ready for a medical treatment, that is, the dialysis fluid in the patient's abdominal cavity 20 is drained into the bag 5 through the abdominal catheter 1, transfer tube 3, and the bag tube 6.

After the fluid has been collected, the transfer tube 3 is again blocked by the clamp 31 and the bag tube 6 is sealed and cut as previously described. The bag 5 full of the used fluid is separated and the fluid is drained.

The transfer tube 3 from which the drainage bag 5 has been separated has connected thereto the protective accessary 7 in the form of the remaining section of bag tube. Therefore, the tube interior is kept sterile until a next infusion.

The next infusion may be carried out by disconnecting the protective accessary 7 from the transfer tube 3 and connecting a bag tube 6 of a new infusion bag 5.

In the conventional procedure, the transfer tube and the bag tube are disconnected and a separate protective accessary is connected to the transfer tube, leaving the risk of bacterial entry during protective accessary connection. In contrast, the method of the present invention allows the unnecessary bag 5 to be separated from the transfer tube 3 while maintaining the connection between the transfer tube 3 and the bag tube 6 (more exactly, between the first and second connectors 4 and 9), thereby substantially eliminating the risk of bacterial entry. There are only two chances of bacterial entry into the tubes during one cycle from the infusion of dialysis fluid to a subsequent infusion of dialysis fluid, the chances being at the time of connection of infusion and drainage bags. That is, the bacterial entry chances are minimized. Even during connection of infusion and drainage bags, bacterial entry can hardly happen at all since connection of the first and second connectors 4 and 9 is done in a flame.

The medical container replacement method of the present invention is applicable to not only the single bag system described above, but also the two bag system.

Although the present invention has been described in the context of peritoneal dialysis as typified by CAPD, the range of application of the invention is not limited thereto. For example, the invention is applicable to connection of tubes for dialysis using an artificial kidney, blood transfusion, and fluid transfusion, and all other tubes which require to maintain a sterile condition (independent of the degree of necessity).

The medical container replacement method of the present invention ensures that the tubes are internally maintained in a sterile condition, providing a high degree of safety to a human body. Particularly when the invention is applied to CAPD in which it is critical to maintain a sterile condition, there are obtained great benefits that the patient need not carry an empty bag during dialysis process and the risk of inducing peritonitis due to bacterial infection is minimized.

Although some preferred embodiments have been described, many modifications and variations may be made thereto in the light of the above teachings. It is therefore to be understood that within the scope of the appended claims, the invention may be practiced otherwise than as specifically described.

We claim:

1. In a system comprising (A) a first tube having a first connector attached thereto at one end and (B) a second tube connected to a medical container and having a second connector attached thereto at a free end, both the first and second tubes requiring to be in a sterile condition when connected, a method for replacing a medical container, comprising the steps of:

connecting the first connector to the second connector to provide fluid communication between the first and second tubes for allowing a medical treatment to be carried out, blocking the second tube at one or more positions at the end of medical treatment, and cutting the second tube at a position nearer to the medical container with respect to the blockade nearest to the second connector, the suspending section of the second tube with the second connector kept connected to the first connector serving as an antibacterial protective accessary for maintaining the connector connection in a sterile condition.

2. The method of claim 1 wherein said steps of blocking and cutting the second tube includes forming two blockades in the second tube and cutting the tube between the two blockades.

3. The method of claim 1 wherein said step of blocking the second tube including sealing the second tube by fusion welding.

4. The method of claim 1 wherein said step of blocking the second tube including blocking the second tube by mechanical clamping means.

5. The method of claim 1 wherein the step of connecting the first and second connectors is carried out in a flame.

* * * * *